US00PP37465P3

(12) United States Plant Patent
Elstgeest

(10) Patent No.: US PP37,465 P3
(45) Date of Patent: Jun. 9, 2026

(54) *DIEFFENBACHIA* PLANT NAMED 'ELSTDI0124'

(50) Latin Name: *Dieffenbachia seguine*
Varietal Denomination: ELSTDI0124

(71) Applicant: ELSTGEEST YOUNG PLANTS HOLDING B.V., Rijsenhout (NL)

(72) Inventor: Debbie Elstgeest, Rijsenhout (NL)

(73) Assignee: Elstgeest Young Plant Holding BV, Rijsenhout (NL)

( * ) Notice: Subject to any disclaimer, the term of this patent is extended or adjusted under 35 U.S.C. 154(b) by 0 days.

(21) Appl. No.: 19/344,175

(22) Filed: Sep. 29, 2025

(65) Prior Publication Data

US 2026/0144176 P1 May 21, 2026

(30) Foreign Application Priority Data

Nov. 21, 2024 (QZ) ..... 2024/2732

(51) Int. Cl.
*A01H 5/12* (2018.01)
*A01H 6/10* (2018.01)

(52) U.S. Cl.
USPC ..... Plt./378

(58) Field of Classification Search
USPC ..... Plt./378
CPC ..... A01H 5/12; A01H 5/00; A01H 6/10
See application file for complete search history.

(56) References Cited

U.S. PATENT DOCUMENTS

PP2,869 P * 2/1969 Chaplin ..... Plt./378
PP29,666 P2 * 9/2018 Elstgeest ..... A01H 6/10 Plt./378

* cited by examiner

*Primary Examiner* — June Hwu
(74) *Attorney, Agent, or Firm* — James R. Holm; Plant Novelty Rights, LLC

(57) ABSTRACT

A new and distinct *Dieffenbachia* plant named 'ELSTDI0124' particularly distinguished by a bushy, upright and compact growth habit, dark green foliage with broad and irregular yellow-green central variegation extending towards the leaf margins, and prolific lateral shoot production, which makes it well-suited for commercial vegetative propagation.

2 Drawing Sheets

Figure 1:
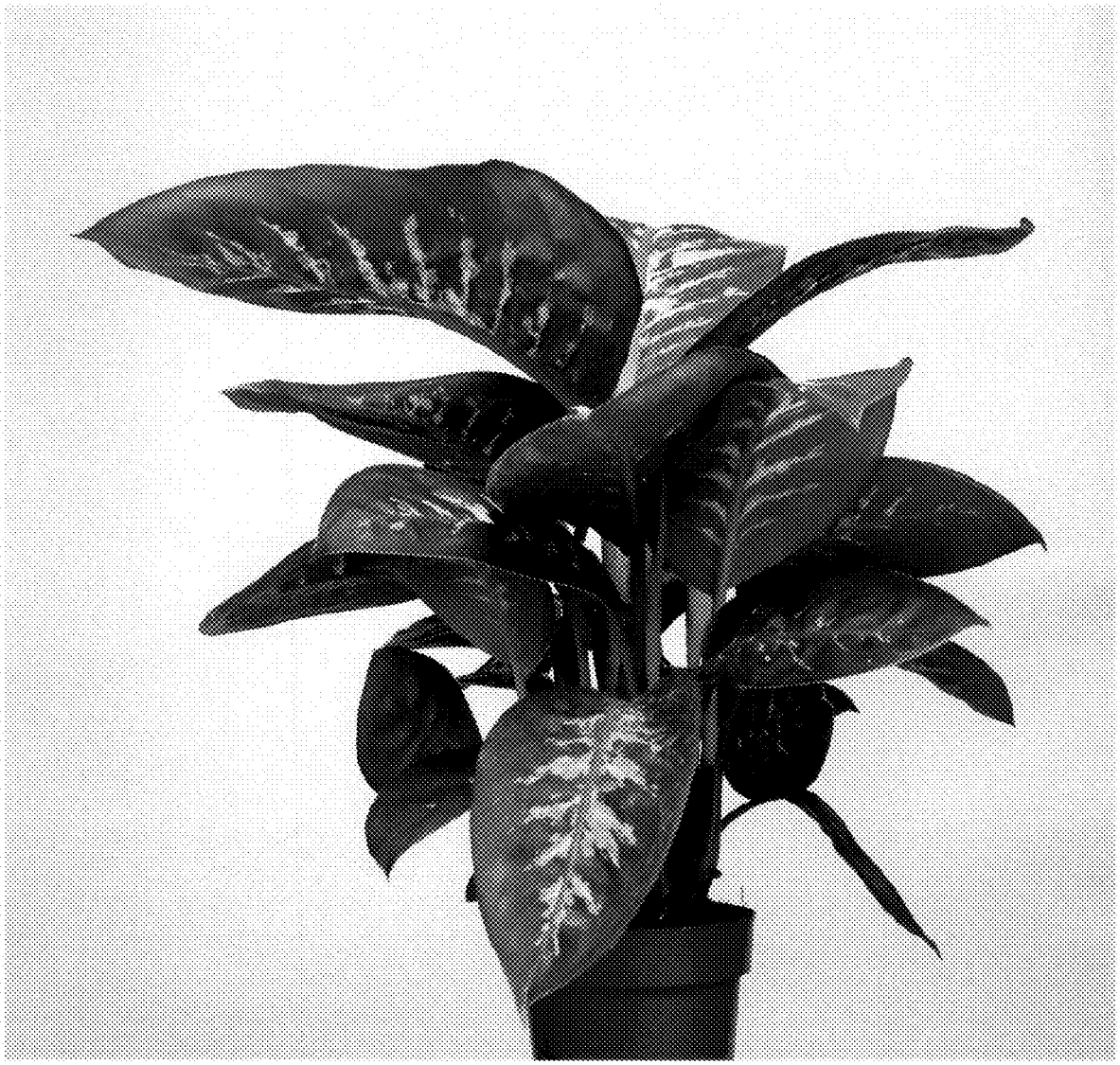

Genus and species: *Dieffenbachia seguine.*
Variety denomination: 'ELSTDI0124'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date. This application claims priority to CPVO application no. 2024/2732 filed on Nov. 21, 2024.

BACKGROUND OF THE NEW PLANT

The present invention comprises a new and distinct variety of *Dieffenbachia* plant, botanically known as *Dieffenbachia seguine*, and hereinafter referred to by the variety name 'ELSTDI0124'.

The new *Dieffenbachia* cultivar 'ELSTDI0124' is a product of a planned breeding program located in Rijsenhout, The Netherlands. The new cultivar is a naturally occurring branch mutation of the *Dieffenbachia* cultivar 'REEVA' (U.S. Plant Pat. No. 29,666). Several mutations were selected by the inventor from the parent stock 'REEVA' for a period of more than one year. The mutations were propagated from cuttings and grown to observe uniformity, stability and distinctness as well as their commercial potential. From amongst these mutations, 'ELSTDI0124' was selected for further propagation and commercialization in November 2023 based on its unique plant shape, the attractiveness of its foliage color, its superior growth rate, its ease of propagation and multiplication, and its uniformity.

The new *Dieffenbachia* cultivar was first reproduced asexually using vegetative meristem tip cuttings in November 2023 in Rijsenhout, The Netherlands. Asexual propagation by vegetative meristem tip cuttings and tissue culture of the new variety has shown that the unique features of the new variety are stable and reproduced true-to-type to date through six successive generations.

SUMMARY OF THE INVENTION

The new *Dieffenbachia* cultivar 'ELSTDI0124' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Dieffenbachia* cultivar. The combination of these characteristics distinguishes 'ELSTDI0124' as a new and distinct variety of *Dieffenbachia.*

1. *Dieffenbachia* 'ELSTDI0124' exhibits a bushy, upright and compact growth habit.
2. *Dieffenbachia* 'ELSTDI0124' exhibits dark green foliage with broad and irregular yellow-green central variegation extending towards the leaf margins.
3. *Dieffenbachia* 'ELSTDI0124' exhibits prolific lateral shoot production, which makes it well-suited for commercial vegetative propagation.

DESCRIPTION OF THE PHOTOGRAPHS

This new *Dieffenbachia* cultivar is illustrated by the accompanying-colored photographs which show the overall appearance and distinct characteristics of the plant. The colors shown are as true as can be reasonably obtained by conventional photographic procedures. The photographs are of 12-month-old plants grown in a 12-centimeter circular container in a conventional glass greenhouse in Rijsenhout, The Netherlands. Colors in the photographs may differ slightly from the color values cited in the botanical description which accurately describes the colors of the new variety.

FIG. 1. shows the overall plant form and foliage of 'ELSTDI0124'.

Figure 2:
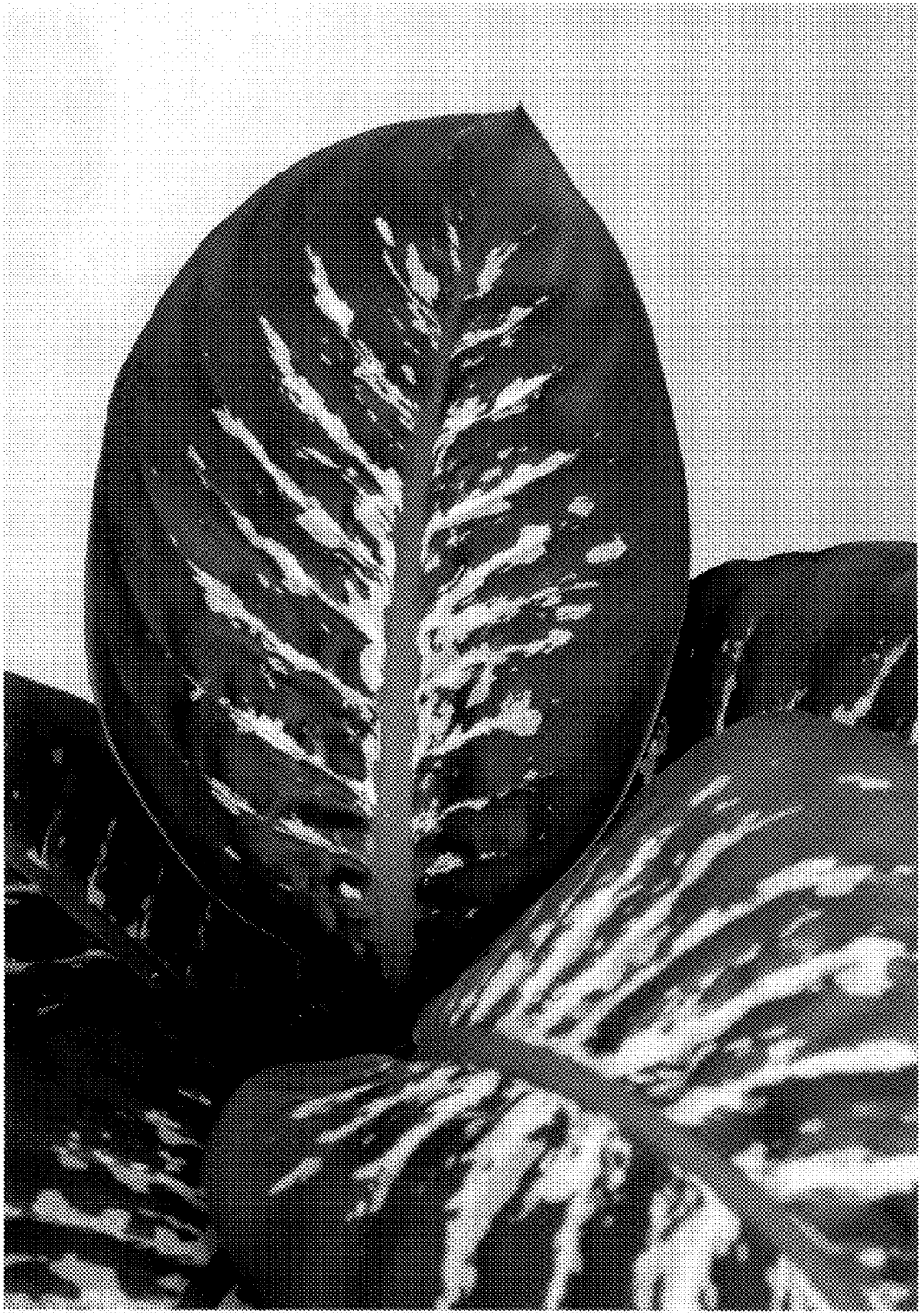

FIG. 2. shows a close-up of a typical leaf of 'ELSTDI0124'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional glass greenhouse located in Rijsenhout, The Netherlands with an average day and night temperature of 19° C. to 21° C. Plants were grown under normal daytime light levels with no artificial supplemental lighting provided. Detailed descriptions were taken in November 2024 from 12-month-old plants grown in 12-centimeter circular containers. Measurements and numerical values represent averages of typical plant types.

DETAILED BOTANICAL DESCRIPTION

Classification:

*Family*.—Araceae.

*Botanical*.—*Dieffenbachia seguine*.

*Denomination*.—'ELSTDI0124'.

General description:

*Plant type*.—Tropical perennial for use as a potted plant.

*Crop time*.—Approximately 26 weeks from propagation to a saleable plant.

*Approximate container size and/or cropping system*.—12.0 cm or larger pots.

*Growth habit*.—Upright.

*Overall plant shape*.—Broad obovate to broad oblong.

*Height from soil level to top of foliar plane*.—31.8 cm.

*Plant diameter or area of spread*.—50.3 cm.

*Growth rate*.—Moderate.

*Plant vigor*.—Moderate to high.

*Branching habit*.—Basal branching with few lateral branches.

*Propagation type*.—Vegetative meristem tip cuttings and tissue culture.

Branch description:

*Number of primary branches or stems per plant*.—Average 6.

*Number of secondary branches or stems per plant*.—Average 2.

*Main branch length*.—Average 11.9 cm.

*Main branch diameter*.—Average 2.2 cm, varying between 1.7 cm and 3.0 cm.

*Main branch internode length*.—Average 2.1 cm.

*Stem appearance and shape*.—Rounded.

*Stem luster*.—Slightly glossy.

*Stem aspect/angle from vertical*.—Average 0°, near vertical.

*Stem strength*.—Strong.

*Stem color*.—Developing stems: A blend of 143B and 143C (green). Mature stems: 137B and 137C (green). Internodes: 137B and 137C (green).

*Pubescence*.—Not present.

Root description: Fleshy.

*Diameter*.—Average 0.3 cm.

*Branching habit*.—Moderately branched.

*Density*.—Moderate.

*Texture*.—Dense and very short pubescence.

*Color*.—158C and 158D (yellow-white).

*Distribution in soil profile*.—Moderately deep.

Foliage description:

*Arrangement*.—Alternate, simple.

*Quantity of leaves per main stem*.—Average of 7.

*Lamina*.—Shape: Ovate. Length: Average 23.5 cm. Width: Average 14.4 cm. Aspect: Slightly carinate. Apex shape: Short apiculate. Base shape: Truncate. Margins: Entire, very slightly undulate to non-undulate. Texture (both upper and lower surfaces): Smooth, glabrous. Pubescence: Not present. Luster: Upper surface: Matte. Lower surface: Very slightly glossy. Color: Juvenile foliage: Upper surface: Slightly darker than 143A (green), areas adjacent to the secondary veins irregularly marbled and blotched with 145A to 145C (yellow-green). Primary vein: 143B (green). Secondary veins: 150D (yellow-green) and lighter. Lower surface: 137D and 138B (green), areas adjacent to the secondary veins irregularly marbled and blotched with 145A to 145D (yellow-green), 150D (yellow-green) and lighter, with a blend of 150D and 157D (yellow-green). Primary vein: 147D (yellow green). Secondary veins A blend of 150D (yellow-green) and 157D (green-white). Mature foliage: Upper surface: A blend of NN137A (green) and 147A (yellow-green), areas adjacent to the secondary veins irregularly marbled and blotched with 144A to 144D (yellow-green) and 145A to 145C (yellow-green). Primary vein: 137B (green). Secondary veins: 145A to 145D (yellow-green). Lower surface: NN137C (green), areas adjacent to the secondary veins irregularly marbled and blotched with 145A to 145B (yellow-green). Primary vein: 143C (green). Secondary veins: 143A (green). Venation pattern: Pinnate.

*Petiole*.—Length: 11.8 cm. Diameter: U-shaped on the upper side, average 0.7 cm in diameter horizontally, and average 0.8 cm in diameter vertically. Texture: Smooth, glabrous. Luster (both upper and lower surfaces): Very slightly glossy. Strength: Strong. Color: Upper surface: 137A (green). Lower surface: 138B (green). Base: Winged, transforming into sheaths at the base of the petiole. Sheath length: Average 9.0 cm. Sheath width: Average 1.5 cm. Sheath color: Upper surface: 137C (green), fading to 143A (green) at the margins. Lower surface: A blend of 143A and 143B (green).

Inflorescence: None observed to date.

Heat tolerance: At least tolerant to temperatures up to 40 degrees Celsius.

Cold tolerance: At least hardy to USDA zone 10.

USDA hardiness zones: Zones 10 to 13.

Rain tolerance: Moderate.

Wind tolerance: Low to Moderate.

Disease and pest tolerance: No claims are made to any superior disease or insect resistance or tolerance.

COMPARISON WITH THE PARENT PLANT

The new *Dieffenbachia* cultivar 'ELSTDI0124' can be distinguished from its progenitor or parent *Dieffenbachia* cultivar 'REEVA' in the following characteristics described in Table 1 below.

TABLE 1

| Characteristic | 'ELSTDI0124' | 'REEVA' |
|---|---|---|
| Plant habit. | Upright, compact and moderately vigorous growth. | Upright, more spreading growth habit. |
| Plant height at 12 months from cuttings. | Shorter. | Taller. |
| Leaf length. | Medium to large. | Larger. |
| Leaf width. | Narrower. | Broader. |
| Leaf shape. | Elliptic to ovate with an acuminate apex. | Ovate with a more rounded apex. |
| Leaf color (upper surface). | Dark green with a broader central variegation of yellow-green. | Medium green with narrower, more defined variegation of yellow-green. |
| Leaf color (lower surface). | Green. | Light green. |
| Variegation pattern. | Broad with an irregular central zone extending towards the margins. | Narrower with a more symmetrical central zone. |

TABLE 1-continued

| Characteristic | 'ELSTDI0124' | 'REEVA' |
|---|---|---|
| Petiole length and color. | Shorter, green with light speckling. | Longer, green with stronger speckling. |
| Internode length. | Shorter, contributing to its compact habit. | Longer, contributing to taller and more open plant habit. |

COMPARISON WITH RELATED KNOWN VARIETY

The new *Dieffenbachia* cultivar 'ELSTDI0124' can be distinguished from the related known variety of *Dieffenbachia* cultivar 'Tropic Snow' (unpatented) in the following characteristics described in Table 2 below.

TABLE 2

| Characteristic | 'ELSTDI0124' | 'Tropic Snow' |
|---|---|---|
| Plant habit. | Upright, compact and moderately vigorous growth. | Upright, more open and vigorous growth. |
| Leaf length. | Medium to large. | Larger. |
| Leaf width. | Narrower. | Broader. |
| Leaf shape. | Elliptic to ovate with an acuminate apex. | Ovate with a more rounded base. |
| Leaf color (upper surface). | Dark green with a broader central variegation of yellow-green. | Dark green with a narrower central variegation of yellow-green. |
| Leaf color (lower surface). | Green. | Light green. |
| Variegation pattern. | Broad with an irregular central zone extending towards the margins. | Narrower, with a more defined central zone with feathered edges. |
| Petiole length and color. | Shorter, green with light speckling. | Longer, green with faint speckling. |
| Internode length. | Shorter, contributing to its compact habit. | Longer, contributing to its taller habit. |

What is claimed is:

1. A new and distinct cultivar of *Dieffenbachia* plant named 'ELSTDI0124', substantially as illustrated and described herein.

* * * * *